United States Patent
Tielemans

(10) Patent No.: US 8,485,198 B2
(45) Date of Patent: Jul. 16, 2013

(54) ORAL ORTHOSIS FOR REDUCING SNORING AND SLEEP APNEA SYMPTOMS

(75) Inventor: Walther M. J. Tielemans, Weert (NL)

(73) Assignee: Walther M. J. Tielemans, Maaseik (BE)

( * ) Notice: Subject to any disclaimer, the term of this patent is extended or adjusted under 35 U.S.C. 154(b) by 64 days.

(21) Appl. No.: 13/100,440

(22) Filed: May 4, 2011

(65) Prior Publication Data

US 2011/0315149 A1    Dec. 29, 2011

Related U.S. Application Data

(63) Continuation of application No. PCT/EP2009/064561, filed on Nov. 3, 2009.

(30) Foreign Application Priority Data

Nov. 4, 2008  (EP) .................................... 08168294

(51) Int. Cl.
*A61F 5/56* (2006.01)
*A61C 5/14* (2006.01)

(52) U.S. Cl.
USPC .......................................... 128/848; 128/859

(58) Field of Classification Search
USPC .............. 128/848, 859–862; 433/6–7, 18–19, 433/21, 24
See application file for complete search history.

(56) References Cited

U.S. PATENT DOCUMENTS 3,132,647 A  5/1964  Corniello
6,408,852 B2  6/2002  Tielemans

FOREIGN PATENT DOCUMENTS

| DE | 4026602 C1 | 11/1991 |
| DE | 10011687 A1 | 11/2000 |
| EP | 0679378 A | 11/1995 |
| WO | 9013276 A | 11/1990 |

OTHER PUBLICATIONS

European Search Report issued by the EPO for EP08168294 on Mar. 17, 2009.
International Search report issued by the EPO for PCT/EP2009/064561 on Feb. 15, 2010.

*Primary Examiner* — Patricia Bianco
*Assistant Examiner* — Ophelia A Hawthorne
(74) *Attorney, Agent, or Firm* — Coraline J. Haitjema; David P. Owen; Hoyng Monegier LLP

(57) ABSTRACT

An oral orthosis for reducing snoring and sleep apnea symptoms includes a maxilla palate plate having a front edge at the front teeth, a back edge at the soft palatum and two sides edges at the molar rows and, attached thereon, a fixing mechanism to fix the plate in the oral cavity and a tongue positioning device. The tongue positioning device includes a pellotte attached to a pellotte bar mounted into the plate with a spring wire engaged to press the pellotte against the tongue when positioned in the oral cavity, wherein the pellotte bar is mounted in the maxilla plate near the front edge of the plate between the molar and cuspidate teeth plus or minus 5 mm.

26 Claims, 2 Drawing Sheets

ORAL ORTHOSIS FOR REDUCING SNORING AND SLEEP APNEA SYMPTOMS

CROSS REFERENCE TO RELATED APPLICATIONS

This application is a continuation of PCT application number PCT/EP2009/064561 filed on 3 Nov. 2009, which claims priority from European patent application number EP 08168294.0 filed on 4 Nov. 2008. Both applications are hereby incorporated by reference in their entireties.

BACKGROUND OF THE INVENTION

1. Field of the Invention

The invention relates to an oral orthosis for reducing snoring and sleep apnea symptoms comprising a maxilla palate plate (1) having a front edge at the front teeth, a back edge at the soft palatum and two sides edges at the molar rows and, attached thereon, fixing means (2) to fix the plate in the oral cavity and a tongue positioning device (3), wherein the tongue positioning device (3) comprises a pellotte (3b) attached to a pellotte bar (3a) mounted into the plate with a spring wire (3c and 3d) engaged to press the pellotte against the tongue when positioned in the oral cavity.

2. Description of the Related Art

DE 40 26602 describes such an oral orthosis for preventing snoring. This orthosis has a small maxilla palate plate to which is attached a spring as the tongue position device. The plate is in the form of an arc fitted to the upper row of teeth. The orthosis is anchored in the oral cavity with wires that attach the plate to the teeth.

In U.S. Pat. No. 6,408,852 an improved oral orthosis is described wherein the blocking of the airway is better prevented by the maxilla plate extending to cover and support also the soft tissue of the palate moll, wherein the extension preferably covers a sensitive area at which the nerve concentration is high and where the plate at that area has an opening or recess to relieve pressure to that sensitive area.

BRIEF SUMMARY OF THE INVENTION

There is a continuous desire to further improve the oral orthosis. However, improvements in reducing sleep apnea and snoring very often have the disadvantage of decreasing client comfort and acceptance. In particular, the extension covering the soft tissue of the palate molle of the oral orthosis described in U.S. Pat. No. 6,408,852 is often refused by patients because it causes a vomiting reflex and often causes sleeping problems. It is therefore an object of the invention to provide an oral orthosis that provides reduced snoring and sleep apnea and at the same time provides increased client comfort and acceptance.

This has been achieved according to the invention, in that the oral orthosis the pellotte bar (3a) is mounted in the maxilla plate near the front edge of the plate between the molar and cuspidate teeth plus or minus 5 mm, wherein the pellotte bar in rest position is at a mounting angle (a) relative to the occlusal plane between 30 and 60, preferably between 40 and 50 degrees, inclined towards the back edge of the plate and wherein the pellotte bar (3a) has a bend near the pellotte towards the front edge with a bend angle (b) between 60 and 30, preferably between 50 and 40 degrees bringing the front surface of the pellotte, when in rest position, at an angle (c) between 70 and 110 degrees, preferably between 80 and 100 degrees (relative to the occlusal plane and back edge).

It was found that with the improved oral orthosis snoring and sleep apnea is more effectively prevented and at the same time has a higher patient acceptance.

BRIEF DESCRIPTION OF THE DRAWINGS

The features and advantages of the invention will be appreciated upon reference to the following drawings, in which.

DESCRIPTION OF ILLUSTRATIVE EMBODIMENTS

The following is a description of certain embodiments of the invention, given by way of example only and with reference to the drawings.

Figure 1:
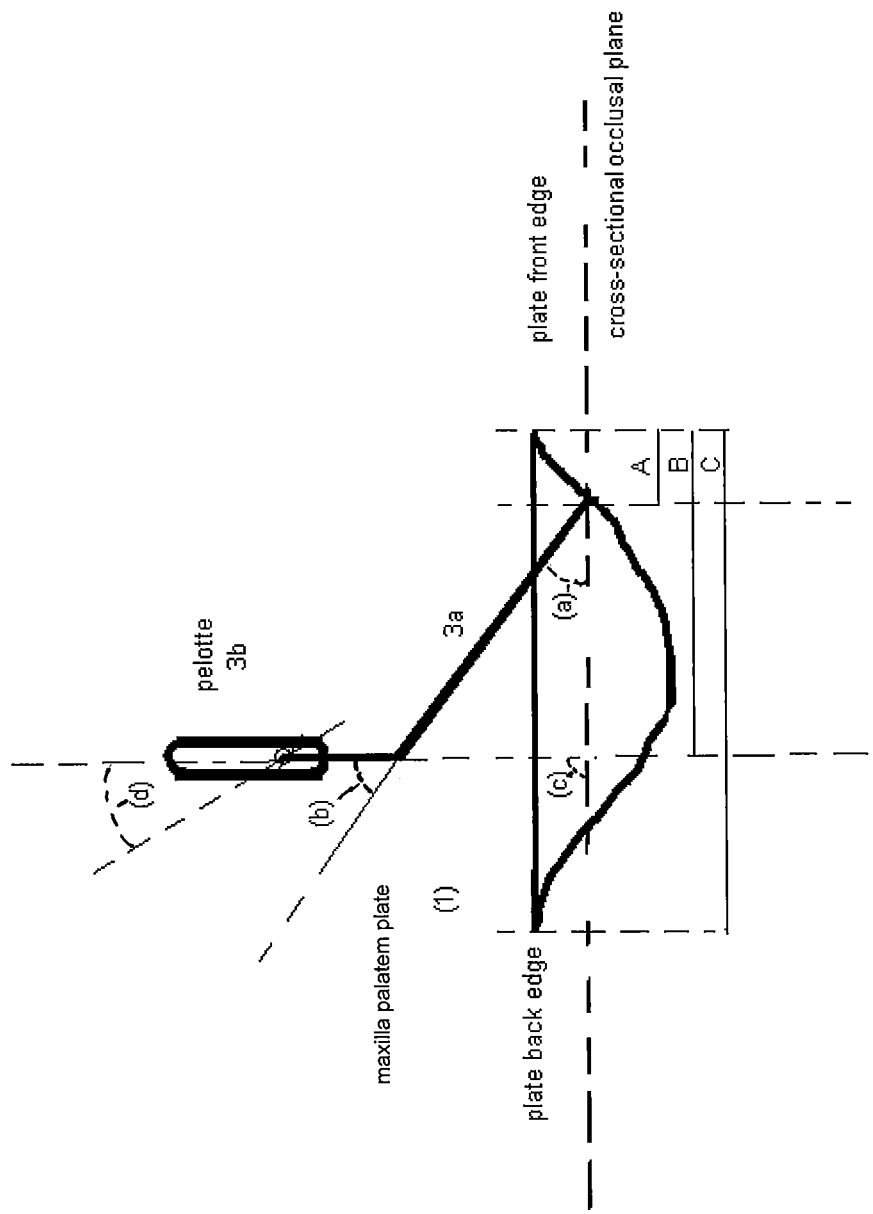
FIG. 1 illustrates a schematic side view of the oral orthosis.

FIG. 1 illustrates a schematic side view of the oral orthosis showing the maxilla palate plate (1) having, when placed in the oral cavity, a front edge at the front teeth and a back edge at the soft palatum and a tongue positioning device 3 comprising the pellotte bar (3a) and the pellotte (3b) mounted to the plate.

Figure 2:
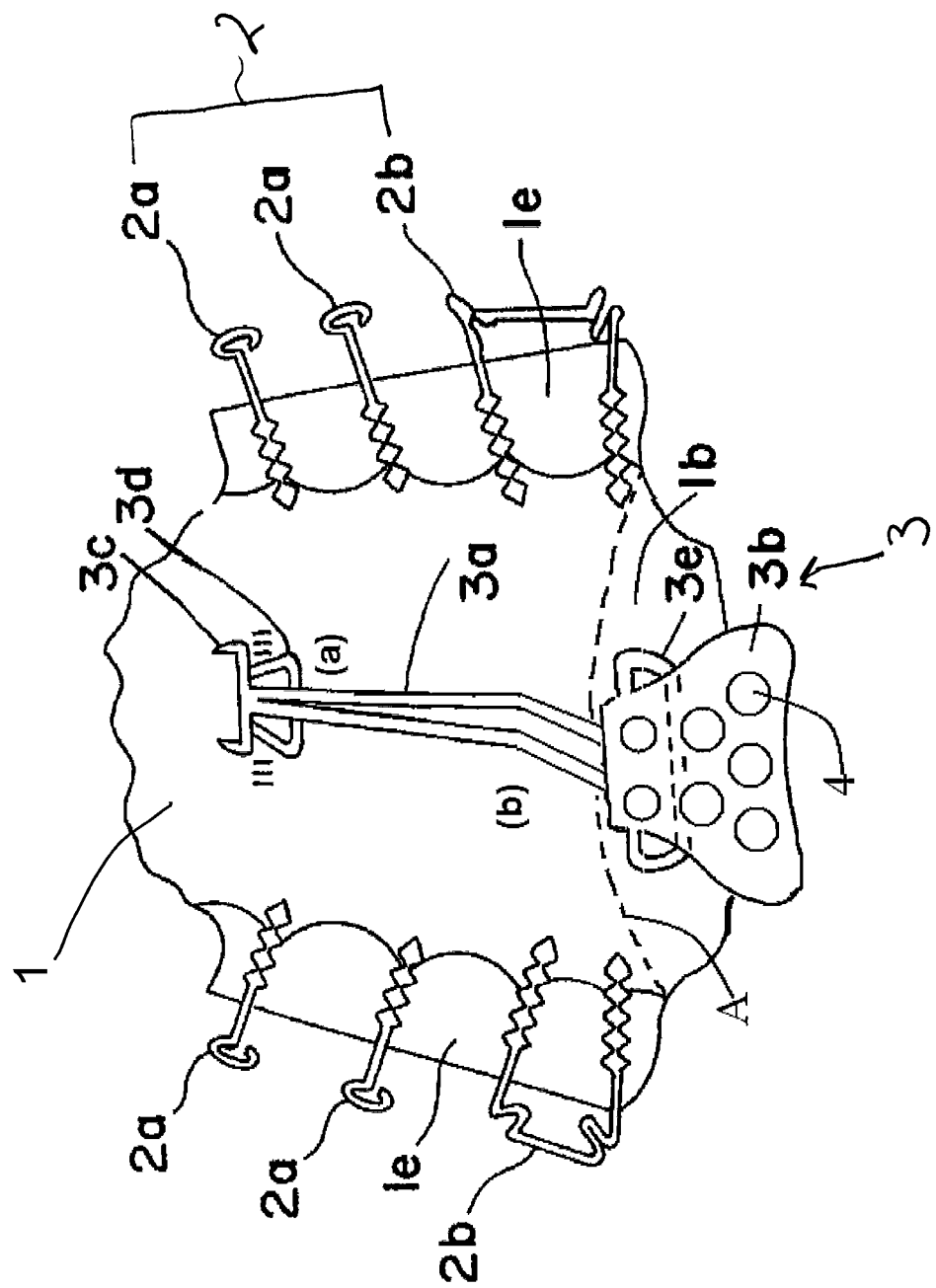
FIG. 2 illustrates a schematic view on the occlusal plane of the oral orthosis.

FIG. 2 illustrates a schematic view on the occlusal plane of the oral orthosis showing the maxilla palate plate (1), the A-line where the hard palate changes to soft palate molle, plate part (1b) extending to support the soft palate molle, plate parts (1e) extending to cover the (pre-)molars, fixing means (2), tongue positioning device 3 comprising the pellotte bar (3a) the pellotte (3b) the spring means (3c, 3d), pellotte mounting axis (3e), the mounting angle (a), the pellotte arm bend angle (b) and finally the cavities in the pellotte surface (4).

In the oral orthosis, the mounting position of the pellotte bar (3a) in the plate, the length of the pellotte bar and the mounting angle (a) and bend angle (b) are chosen in combination such that, when placed in the oral cavity, the pellotte (3b) is at the back of the tongue and the front surface of the pellotte is preferably essentially parallel with the tongue when in high tonus unrelaxed state (head vertically) without exerting significant pressure, such that when the tongue and soft palatum sags back during sleeping (head in horizontal position) the pellotte exerts a forward force pushing the tongue forward and keeping the air duct open.

Evidently, the shape of the maxilla, tongue and oral cavity are different for every patient and the size of the maxilla plate, the position, length and bend angles of the pellotte bar vary for each patient. Apart from that, the perception of discomfort and acceptance of an oral orthosis is different for each patient and may even vary in time for one patient. Therefore each oral orthosis is individual fitted to the patients needs and dimensions vary substantially within the ranges indicated below.

The mounting angle and length of the pellotte arm, the position of the bend and the bend angle is preferably chosen to bring the pellotte behind the A-line (defined as the line where the hard palatum ends and soft palatum begins). Typically, the bend is near the pellotte at about 50% to 90% of the length of the pellotte arm (measured from the connection point of the pellotte arm in the plate to the connection point of the pellotte). The length of the pellotte can range between 3 and 10 cm.

Generally, the pellotte bar (3a) is mounted in the maxilla plate near the front edge of the plate at a distance from the front edge along the maxilla plate between 5 mm and 40 mm, usually between 10 and 35 and most often between 15 and 30 mm, typically between the molar and cuspidate teeth plus or minus 5 mm. Preferably, the pelotte is essentially on the sutura mediana line. In a cross-sectional side view, the pellotte arm is typically mounted at a projected distance (A) from the front edge between 0.1 and 0.5, preferably between 0.2 and 0.4 times the projected distance (C) between the front and back edge. The projected distance is determined in a projection on the occlusal plane, i.e. the plane running between the molars on both sides. The pellotte arm preferably extends to hold the pellotte across a point at a projected distance (B) from the front edge between 0.5 and 0.9, preferably between 0.6 and 0.8 times the projected distance (C) between the front and back edge.

To prevent the tongue from sagging back into the throat it is important that the pellotte has sufficient grip. In U.S. Pat. No. 6,408,852 it is suggested to roughen the surface. It has been found that this is inadequate, in particular in an oral orthosis according to the invention having the particular positioned and shaped tongue positioning device. As a further improvement there is provided an oral orthosis as described in the preamble, in particular an oral orthosis according to the invention, wherein the pellotte has in a front surface thereof (the surface engaging the tongue) one or more, preferably at least 3, cavities, having an equivalent diameter between 2 to 8 mm, preferably between 3 and 5 mm and preferably having a depth between 30 and 60% of the equivalent diameter. Preferably, the one or more cavities are spherical boreholes, preferably half spheres. It was found that the cavities of the specified size match with the structure of the tongue and provide significant better grip. It is believed that the cavities also provide grip by creating a vacuum when the tongue slips from the pellotte. In order to maximise grip it is preferred that the pellotte front surface is maximally covered with said cavities, in particular at least 25%, more preferably at least 50% of the pellotte front surface. For patient that experience lack of comfort from cavities having sharp edges the one or more cavities preferably are spherical boreholes provided with a smoothed edge, preferably by a shallow concentric spherical bore with a larger diameter.

In the oral orthosis according the pellotte ($3b$) is preferably rotatably mounted on pellotte bar ($3a$) on an axis ($3e$) extending through the pellotte wherein the total rotation of the pellotte is restricted to a maximum of 50 degrees and the rotation is blocked between pellotte rotation angle (d) between −20 and +30 degrees, preferably between −5 and 25 degrees. Compared with the mentioned prior art, the pellotte rotation movement is much more restricted to prevent that the tongue slips back in the throat whilst allowing some rotational freedom to accommodate small movements of the tongue for example from swallowing reflexes.

The prior art describes that a good anti-snoring effect is obtained if in the oral orthosis the palate plate (1) extents to cover and support also the soft palate molle (1b) preferably for at least about 30% of the soft palate. The inventor now improved on that by establishing the criteria optimising on one hand the anti-snoring effect and on the other hand the client acceptance. As a further improvement there is provided an oral orthosis as described in the preamble, in particular an oral orthosis according to the invention, wherein the palate plate (1) extents to cover and support also the soft palate molle (1b) for a distance between 5 and 25, preferably between 10 and 20 and more preferably between 12 and 16 mm beyond the A-line.

The inventor further found that the anti-snoring effect improves, without decreasing too much client comfort, if in an oral orthosis as described in the preamble, in particular an oral orthosis according to the invention, the plate (1) extents to cover and support also the soft palate molle (1b) for a distance between 5 and 25 mm beyond the A-line and has, in the part supporting the soft palate two, preferably oval shaped, protuberances acting as pressure points on the soft palate molle both at a position between 0.5 to 3 mm equidistant from the sutura mediana and at a distance from the A line between 3 to 15, preferably 5 to 10 mm. The protuberances are preferably oval shaped, a length of 0.5 to 3 mm and a width of 0.5 to 1.5 mm and protruding about 0.5 to 1.5 mm from the plate surface. This finding is surprising considering that the prior art is quite opposed in proposing an opening to avoid pressurising nerve points.

Further, the inventor found that the anti-snoring effect further improves, without decreasing too much client comfort, if in an oral orthosis as described in the preamble, in particular an oral orthosis according to the invention the plate (1) is provided with locking means such as a locking mechanism to hold the lower jaw, when positioned in the oral cavity, in a protruded position relative to the upper jaw. This creates additional spaces in the oral cavity preventing blocking of the air-duct. The locking means can be metal wire cramps mounted in the maxilla plate to lock to the teeth of the lower jaw in a protruded position and/or can be extensions (1e) of the plate covering the premolar and/or molar sections of the upper jaw and lower jaw, which extensions are moulded to fit both the occlusal profile of the teeth in the upper jaw and of the teeth in the lower jaw in forward position.

The inventor found that an important factor contributing to the perceived discomfort of wearing an oral orthosis is that the orthosis stimulates the production of saliva. The saliva causes a swallowing effect which movement is to some extent restricted by the orthosis, which caused some discomfort. The inventor has solved the problem of excessive saliva production by providing an oral orthosis as described in the preamble, in particular an oral orthosis according to the invention wherein the metal parts, in particular the fixing means (e.g., fixing mechanism) (2), the pellotte bar (3a), the spring wire (3c and 3d) and optional lower jaw locking means are covered with a layer of rhodium. It was further found that this beneficial effect could be best obtained when the metal is surgical steel, preferably class 5 surgical steel, covered directly with a layer of rhodium. Covered directly means "without necessity of an intermediate adhesion layer". This has also an economic advantage. The metal covering can be done by known means, for example by electroplating. The invention also relates to the use of surgical steel, preferably class 5 surgical steel, covered directly with a layer of rhodium, in oral orthosises, for example anti-snoring devices and orthodontic devices.

Thus, the invention has been described by reference to certain embodiments discussed above. It will be recognized that these embodiments are susceptible to various modifications and alternative forms well known to those of skill in the art. Further modifications in addition to those described above may be made to the structures and techniques described herein without departing from the spirit and scope of the invention. Accordingly, although specific embodiments have been described, these are examples only and are not limiting upon the scope of the invention.

What is claimed is:

1. An oral orthosis for reducing snoring and sleep apnea symptoms comprising a maxilla palate plate having a front edge configured to be positioned at the front teeth, a back edge configured to be positioned at the soft palatum and two sides edges configured to be positioned at the molar rows and, attached thereon, fixing mechanism to fix the maxilla palate plate in the oral cavity and a tongue positioning device, wherein the tongue positioning device comprises a pellotte attached to a pellotte bar mounted into the maxilla palate plate with a spring wire engaged to press the pellotte against the tongue when positioned in the oral cavity, wherein the pellotte bar is mounted at a mounting position in the maxilla palate plate near the front edge of the maxilla palate plate between the molar and cuspidate teeth plus or minus 5 ram, wherein the pellotte bar in rest position is at a mounting angle (a) relative to the occlusal plane between 30 and 60 degrees, inclined towards the back edge of the maxilla palate plate and wherein the pellotte bar has a bend near the pellotte towards the front edge with a bend angle (b) between 30 and 60 degrees bringing the front surface of the pellotte, when in rest position, at an angle (c) between 70 and 110 degrees relative to the occlusal plane and back edge.

2. The oral orthosis according to claim 1, wherein the pellotte has in a front surface thereof one or more cavities, having an equivalent diameter between 2 to 8 mm.

3. The oral orthosis according to claim 2, wherein the one or more cavities are spherical boreholes.

4. The oral orthosis according to claim 3, wherein the one or more cavities are half spheres.

5. The oral orthosis according to claim 4, wherein the pellotte is rotatably mounted on pellotte bar on an axis extending through the pellotte wherein the pelotte has a total rotation restricted to a maximum of 50 degrees and the rotation is blocked between pellotte rotation angle (d) between −20 and +30 degrees.

6. The oral orthosis according to claim 5, wherein the pellotte rotation angle is between −5 and 25 degrees.

7. The oral orthosis according to claim 2, wherein the one or more cavities are spherical boreholes having a smoothed edge.

8. The oral orthosis according to claim 7, wherein the spherical boreholes are made by a shallow spherical bore with a larger diameter.

9. The oral orthosis according to claim 5, wherein at least one of: the pellotte has at least three cavities, and the equivalent diameter of the cavities is between 3 and 5 mm, and the depth of the cavities is between 30 and 60% of the equivalent diameter.

10. The oral orthosis according to claim 2, wherein the one or more cavities cover at least 25% of the pellotte front surface.

11. The oral orthosis according to claim 1, wherein the maxilla palate plate is provided with a locking mechanism to hold the lower jaw, when positioned in the oral cavity, in a protruded position relative to the upper jaw.

12. The oral orthosis according to claim 11, wherein the locking mechanism is metal wire cramps mounted to lock to the teeth of the lower jaw in a protruded position.

13. The oral orthosis according to claim 11, wherein the maxilla palate plate has extensions covering at least one of the premolar and molar sections of the upper jaw and lower jaw, which extensions are moulded to fit both the occlusal profile of the teeth in the upper jaw and of the teeth in the lower jaw in forward position.

14. The oral orthosis according to claim 1, wherein the fixing means, pelotte bar and spring wire are metal parts covered with a layer of rhodium to prevent excessive production of saliva during use.

15. The oral orthosis according to claim 14, wherein the metal is surgical steel, covered directly, that is without intermediate adhesion layer, with a layer of rhodium.

16. The oral orthosis according to claim 15, wherein the metal surgical steel is class 5 surgical steel.

17. The oral orthosis according to claim 1, wherein the maxilla palate plate extends for a distance between 5 and 25 mm beyond the line, such that during use, this distance matches where the hard palatum ends and the soft palatum begins.

18. The oral orthosis according to claim 17, wherein the maxilla palate plate extends the distance of 12-16 mm.

19. The oral orthosis according to claim 1, wherein the maxilla palate plate has a part extending beyond a line where the hard palatum ends to support the soft palate during use and in said part has, in the soft palate support two protuberances acting as pressure points on the soft palate molle both at a position between 0.5 to 3 mm equidistant from the sutura mediana and at a distance from the line between 3 to 15 mm.

20. The oral orthosis according to claim 19, wherein the soft palate support protuberances are oval shaped.

21. The oral orthosis according to claim 1, wherein the bend is near the pellotte at 50% to 90% of the length of the pellotte arm measured from the connection point of the pellotte arm in the plate to the connection point of the pellotte.

22. The oral orthosis according to claim 1, wherein the pellotte is behind a line where the hard palatum ends and soft palatum begins.

23. The oral orthosis according claim 1, wherein when placed in the oral cavity, the pellotte is at the back of the tongue and the pellotte has a front surface being essentially parallel with the tongue when in high tonus unrelaxed state without exerting significant pressure, such that when the tongue and soft palatum sags back during sleeping the pellotte exerts a forward force pushing the tongue forward.

24. The oral orthosis according to claim 1, wherein the pellotte bar in rest position is at the mounting angle (a) relative to the occlusal plane between 40 and 50 degrees.

25. The oral orthosis according to claim 1, wherein the pellotte bar has a bend near the pellotte towards the front edge of the oral orthosis with the bend angle (b) between 40 and 50 degrees.

26. The oral orthosis according to claim 1, wherein the pellotte has a front surface, when in rest position, is at an angle (c) between 80 and 100 degrees relative to the occlusal plane and back edge.

\* \* \* \* \*